(12) United States Patent
Vokrot et al.

(10) Patent No.: US 11,369,446 B2
(45) Date of Patent: Jun. 28, 2022

(54) PEDAL CONTROL FOR ROBOTIC SURGICAL SYSTEMS

(71) Applicant: Covidien LP, Mansfield, MA (US)

(72) Inventors: Peter Vokrot, Malden, MA (US);
William Peine, Ashland, MA (US);
Jared Farlow, Los Angeles, CA (US);
Robert Pierce, Franklin, MA (US)

(73) Assignee: Covidien LP, Mansfield, MA (US)

( * ) Notice: Subject to any disclaimer, the term of this patent is extended or adjusted under 35 U.S.C. 154(b) by 284 days.

(21) Appl. No.: 16/614,746

(22) PCT Filed: May 17, 2018

(86) PCT No.: PCT/US2018/033080
§ 371 (c)(1),
(2) Date: Nov. 18, 2019

(87) PCT Pub. No.: WO2018/217522
PCT Pub. Date: Nov. 29, 2018

(65) Prior Publication Data
US 2020/0188048 A1 Jun. 18, 2020

Related U.S. Application Data

(60) Provisional application No. 62/510,502, filed on May 24, 2017.

(51) Int. Cl.
*A61B 34/35* (2016.01)
*A61B 34/00* (2016.01)
(Continued)

(52) U.S. Cl.
CPC .............. *A61B 34/35* (2016.02); *A61B 17/00* (2013.01); *A61B 34/25* (2016.02); *A61B 34/37* (2016.02);
(Continued)

(58) Field of Classification Search
CPC ......... A61B 34/35; A61B 34/37; A61B 34/30; A61B 34/25; A61B 17/00;
(Continued)

(56) References Cited

U.S. PATENT DOCUMENTS 4,523,911 A * 6/1985 Braetsch .............. A61C 1/0023
251/295
4,983,901 A 1/1991 Lehmer
(Continued)

FOREIGN PATENT DOCUMENTS

| CA | 2546702 A1 | 6/2005 |
|----|-----------|--------|
| EP | 1116477 A1 | 7/2001 |

OTHER PUBLICATIONS

Extended European Search Report dated Mar. 18, 2021 corresponding to counterpart Patent Application EP 18806160.0.
(Continued)

*Primary Examiner* — Aaron F Roane
(74) *Attorney, Agent, or Firm* — Carter, DeLuca & Farrell LLP (57) ABSTRACT

A foot pedal for a user interface of a robotic surgical system includes a frame, a lever, and a sensor system. The lever is coupled to the frame and is pivotable relative to the frame between an initial position and a fully actuated position. The sensor system has a first element associated with the frame and a second element that is associated with the lever. The sensor system is configured to determine the position of the lever relative to the frame.

20 Claims, 8 Drawing Sheets

(51) Int. Cl.
*A61B 34/37* (2016.01)
*A61B 17/00* (2006.01)
*A61B 90/00* (2016.01)

(52) U.S. Cl.
CPC ............... *A61B 2017/00199* (2013.01); *A61B 2017/00212* (2013.01); *A61B 2017/00973* (2013.01); *A61B 2017/00977* (2013.01); *A61B 2090/0807* (2016.02)

(58) Field of Classification Search
CPC .. A61B 2090/0807; A61B 2017/00199; A61B 2017/00212; A61B 2017/00973; A61B 2017/00977
USPC ............................................................ 606/1
See application file for complete search history.

(56) References Cited

U.S. PATENT DOCUMENTS

| | | | | |
|---|---|---|---|---|
| 5,422,521 | A * | 6/1995 | Neer | A61C 1/0023 307/119 |
| 6,017,354 | A * | 1/2000 | Culp | A61B 17/32002 606/170 |
| 6,318,208 | B1 | 11/2001 | Thongs, Jr. et al. | |
| 8,828,023 | B2 | 9/2014 | Neff et al. | |
| 2004/0035242 | A1 | 2/2004 | Peterson et al. | |
| 2004/0115591 | A1* | 6/2004 | Warner | A61C 1/0023 433/98 |
| 2004/0193182 | A1* | 9/2004 | Yaguchi | A61F 9/00745 606/128 |
| 2010/0198200 | A1* | 8/2010 | Horvath | A61B 17/00 606/10 |
| 2010/0228249 | A1 | 9/2010 | Mohr et al. | |
| 2011/0106068 | A1 | 5/2011 | Horvath et al. | |
| 2015/0051607 | A1 | 2/2015 | Hajishah et al. | |
| 2015/0257814 | A1* | 9/2015 | Berry | G06F 3/04847 606/34 |
| 2017/0136159 | A1 | 5/2017 | Mallough | |

OTHER PUBLICATIONS

International Search Report dated Sep. 4, 2018 and Written Opinion completed Sep. 3, 2018 corresponding to counterpart Int'l Patent Application PCT/US2018/033080.

Extended European Search Report dated Feb. 1, 2021 corresponding to counterpart Patent Application EP 18806539.5.

* cited by examiner

PEDAL CONTROL FOR ROBOTIC SURGICAL SYSTEMS

CROSS-REFERENCE TO RELATED APPLICATIONS

This application is a National Stage Application of PCT/US2018/033080, filed May 17, 2018 under 35USC § 371 (a), which claims benefit of and priority to U.S. Provisional Patent Application Ser. No. 62/510,502 filed May 24, 2017, the disclosures of each of the above-identified applications are hereby incorporated by reference in their entirety.

BACKGROUND

Robotic surgical systems have been used in minimally invasive medical procedures. During a medical procedure, the robotic surgical system is controlled by a surgeon interfacing with a user interface. The user interface allows the surgeon to manipulate an end effector that acts on a patient. The user interface includes an input controller that is moveable by the surgeon to control the robotic surgical system.

The input controller of the user interface includes an input device or handle that is supported on a gimbal that is engaged by a surgeon to allow the surgeon to manipulate the end effector. To activate some functions of the end effector, a foot pedal may need to be depressed. Generally, the foot pedals are assigned to individual handles.

To increase flexibility of the robotic surgical system, it would be advantageous for the foot pedals to be assignable to one or more input handles during the same surgical procedure.

SUMMARY

This disclosure relates generally to a user interface for actuating a function of a tool of a surgical robot. The user interface includes first and second input handles and a foot pedal. The foot pedal is selectively associatable to each of the first and second input handles and the tool of the surgical robot is configured to actuate in response to a control of an associated input handle being actuated at the same time the foot pedal is depressed.

In accordance with the present disclosure, a user interface for a robotic surgical system includes a processing unit, an input handle, and a foot pedal. The input handle includes an actuation control that has an actuated position. In the actuated position, the input handle transmits a handle signal to the processing unit. The foot pedal includes an actuation switch that has an actuated position. In the actuated position, the foot pedal transmits a foot signal to the processing unit. The processing unit is configured to associate the input handle with the foot pedal in response to the actuation control being actuated and released. The processing unit is also configured to generate a control signal configured to actuate a tool of the robotic system that is associated with the input handle when the processing unit simultaneously receives a handle signal from the associate input handle and a foot signal from the foot pedal.

In aspects, the foot pedal has an initial position and includes a lockout mechanism. The lockout mechanism may have a locked configuration where the lockout mechanism prevents movement of the foot pedal from the initial position to the actuated position. The lockout mechanism may also have an unlocked configuration where the lockout mechanism allows movement of the foot pedal between the initial position and the actuated position.

In some aspects, the lockout mechanism includes a motor and a pin that extends from the motor. The lockout mechanism may be configured to move the foot pedal towards the initial position as the lockout mechanism transitions from the unlocked configuration to the locked configuration. The pin may be configured to engage the foot pedal to move the foot pedal towards the initial position as the lockout mechanism transitions from the unlocked configuration to the locked configuration.

In certain aspects, the foot pedal includes a frame and a lever pivotally supported by the frame. The lever may include a tongue that extends towards the frame. The lockout mechanism can have a locked configuration where the pin is engagable by the tongue to prevent the lever of the foot pedal from pivoting from the initial position to the actuated position. The lever of the foot pedal can have a locked out position that is between the initial position and the actuated position. In the locked out position, the tongue may engage the pin such that the lever is prevented from pivoting towards the actuated position.

In particular aspects, when the lockout mechanism transitions from the unlocked configuration towards the locked configuration, with the lever of the foot pedal between the locked out position and the actuated position, the tongue prevents the lockout mechanism from achieving the locked configuration. The motor may include a driveshaft that is configured to rotate the pin between the locked configuration and the unlocked configuration. The foot pedal may include an activation sensor and have a locked out position between the initial position and the actuated position. The activation sensor may be configured to send an activation signal to the processing unit when the activation sensor is contacted by the foot pedal or the lockout mechanism. The processing unit may be configured to transmit a feedback signal in response to the activation signal. The user interface may provide feedback in response to the feedback signal. The foot pedal can be biased towards the initial position.

In another aspect of the present disclosure, a foot pedal of a user interface for a robotic surgical system includes a frame, a lever, an actuation switch, and a lockout mechanism. The lever is supported by the frame and is pivotal between an initial position and an actuated position. The actuation switch is configured to transmit a signal when the lever is in the actuated position. The lockout mechanism has a locked configuration where the lockout mechanism prevents a movement of the lever from the initial position to the actuated position.

In aspects, the lockout mechanism includes a motor and a pin. The motor may be configured to rotate the pin. Additionally or alternatively, the motor may be configured to extend the pin away from the motor. The pin can be configured to pivot the lever towards the initial position as the lockout mechanism transitions from the unlocked configuration to the locked configuration.

In another aspect of the present disclosure, a method of actuating a tool of a robotic surgical system that has a user interface includes associating an input handle of the user interface with a foot pedal of the user interface and actuating the tool by substantially simultaneously depressing the foot pedal to an actuated position and actuating a trigger of the associated input handle.

In aspects, the method includes disassociating the input handle from the foot pedal by associating another input handle of the user interface with the foot pedal or releasing the trigger of the associate input handle for a predetermined amount of time.

In another aspect of the present disclosure, a foot pedal for a user interface of a robotic surgical system includes a frame, a lever, and a sensor system. The lever is coupled to the frame and is pivotable relative to the frame between an initial position and a fully actuated position. The sensor system has a first element that is associated with the frame and a second element that is associated with the lever. The sensor system is configured to determine the position of the lever relative to the frame.

In aspects, the foot pedal includes an actuation switch. The lever may be configured to depress the actuation switch when the lever is in the fully actuated position.

In some aspects, the first element is disposed within the frame. The second element may be disposed within the lever.

In certain aspects, the frame includes an indication light that is configured to emit light from the frame. The indication light may be configured to vary a property of the emitted light in response to the position of the lever relative to the frame. The property of the emitted light may be a color, an intensity, and/or a pattern.

In particular aspects, the sensor system is a capacitive displacement system. The second element may be formed of a conductive material.

In aspects, the second element is configured to generate a magnetic field or an electric field and the first element is configured to detect the magnetic field or the electrical field.

In another aspect of the present disclosure, a user interface of a robotic surgical system includes a processing unit, an input handle, and a foot pedal. The input handle includes an actuation control that has an activated position in which the input handle transmits a handle signal to the processing unit. The foot pedal includes a frame, a lever, and a sensor system. The lever is coupled to the frame and is pivotable relative to the frame between an initial position and a fully actuated position. The sensor system has a first element that is associated with the frame and a second element associated with the lever. The sensor system is configured to transmit the position of the lever relative to the frame to the processing unit.

In aspects, the foot pedal includes an actuation switch. The lever may be configured to depress the actuation switch when the lever is in the fully actuated position. The actuation switch may be configured to transmit an actuation signal to the processing unit when the actuation switch is depressed.

In some aspects, the foot pedal may include a lockout mechanism that has a locked configured in which the lockout mechanism prevents movement of the foot pedal from the initial position to the fully actuated position and an unlocked configuration in which the lockout mechanism allows movement of the foot pedal between the initial position and the fully actuated position. The frame may include an indication light that is configured to emit light from the frame.

In another aspect of the present disclosure, a method of manipulating a robotic surgical system that has a user interface including depressing a lever of a foot pedal of the user interface towards a frame of the foot pedal form an initial position towards a fully actuated position and visualizing an indication light of the frame to determine the position of the lever relative to the frame.

In aspects, the method includes associating an input handle of the user interface with the foot pedal of the user interface.

In some aspects, visualizing the indication light of the frame includes a sensor system of the foot pedal determining a position of the lever relative to the frame. The indication light may vary a property of light emitted from the indication light in response to the position of the lever determined by the sensor system. Determining the position of the lever relative to the frame may include a first element associated with the frame detecting a position of a second element associated with the lever. Detecting the position of the second element may include the first element being a capacitive sensor that detects the position of the second element. Detecting the position of the second element may include detecting a magnetic field generated by the second element.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Figure 1:
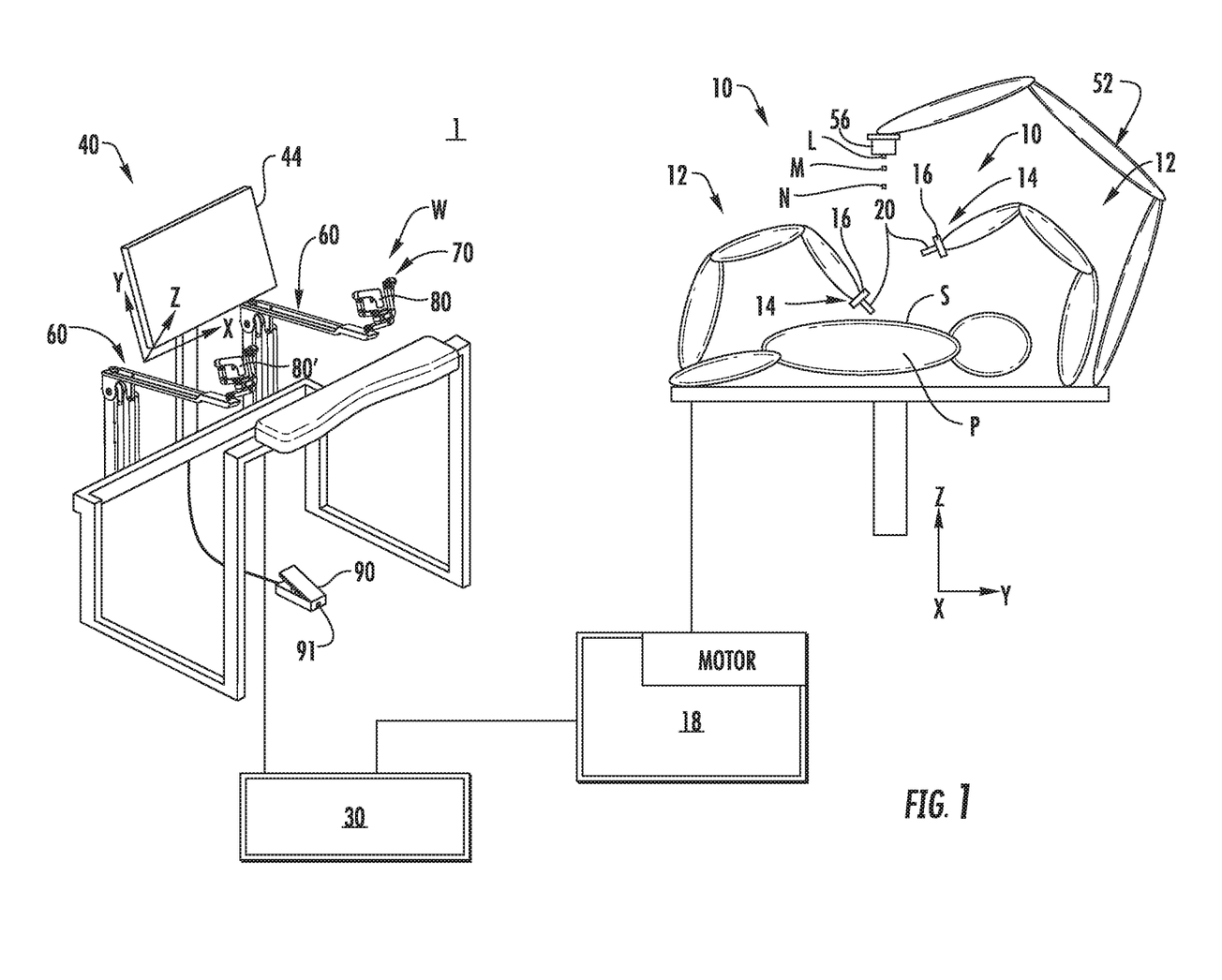
FIG. 1 is a schematic illustration of a user interface and a robotic system in accordance with the present disclosure.

Referring to FIG. 1, a robotic surgical system 1 is shown generally as a robotic system 10, a processing unit 30, and a user interface 40. The robotic system 10 generally includes linkages 12 and a robot base 18. The linkages 12 moveably support an end effector or tool 20 which is configured to act on tissue. The linkages 12 may be in the form of arms or links each having an end 14 that supports an end effector or tool 20 which is configured to act on tissue. In addition, the ends 14 of the linkages 12 may include an imaging device 16 for imaging a surgical site "S". The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the ends 14 of the linkages 12 and/or include data captured by imaging devices that are positioned about the surgical theater (e.g., an imaging device positioned within the surgical site "S", an imaging device positioned adjacent the patient "P", imaging device 56 positioned at a distal end of an imaging linkage 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user interface 40 also includes input handles 80, 80' attached to gimbals 70 which allow a clinician to manipulate the robotic system 10 (e.g., move the linkages 12, the ends 14 of the linkages 12, and/or the tools 20). Each of the gimbals 70 is in communication with the processing unit 30 to transmit control signals thereto and to receive feedback signals therefrom. Additionally or alternatively, each of the input handles 80, 80' may include control interfaces which allow the surgeon to actuate (e.g., clamp, grasp, fire, open, close, rotate, thrust, slice, etc.) the tools 20 supported at the ends 14 of the linkages 12. The user interface 40 further includes a foot pedal 90 that may be used with one or both of the input handles 80, 80' to control actuation of the tools 20.

Each of the gimbals 70 is moveable to move the ends 14 of the linkages 12 within a surgical site "S". The three-dimensional images on the display device 44 are orientated such that movement of the gimbals 70 moves the ends 14 of the linkages 12 as viewed on the display device 44. It will be appreciated that the orientation of the three-dimensional images on the display device 44 may be mirrored or rotated relative to view from above the patient "P". In addition, it will be appreciated that the size of the three-dimensional images on the display device 44 may be scaled to be larger or smaller than the actual structures of the surgical site "S" permitting the surgeon to have a better view of structures within the surgical site "S". As the gimbal 70 is moved, the tools 20 are moved within the surgical site "S". Movement of the tools 20 may also include movement of the ends 14 of the linkages 12 which support the tools 20.

For a detailed discussion of the construction and operation of a robotic surgical system 1, reference may be made to U.S. Pat. No. 8,828,023, the entire contents of which are incorporated herein by reference.

Figure 2:
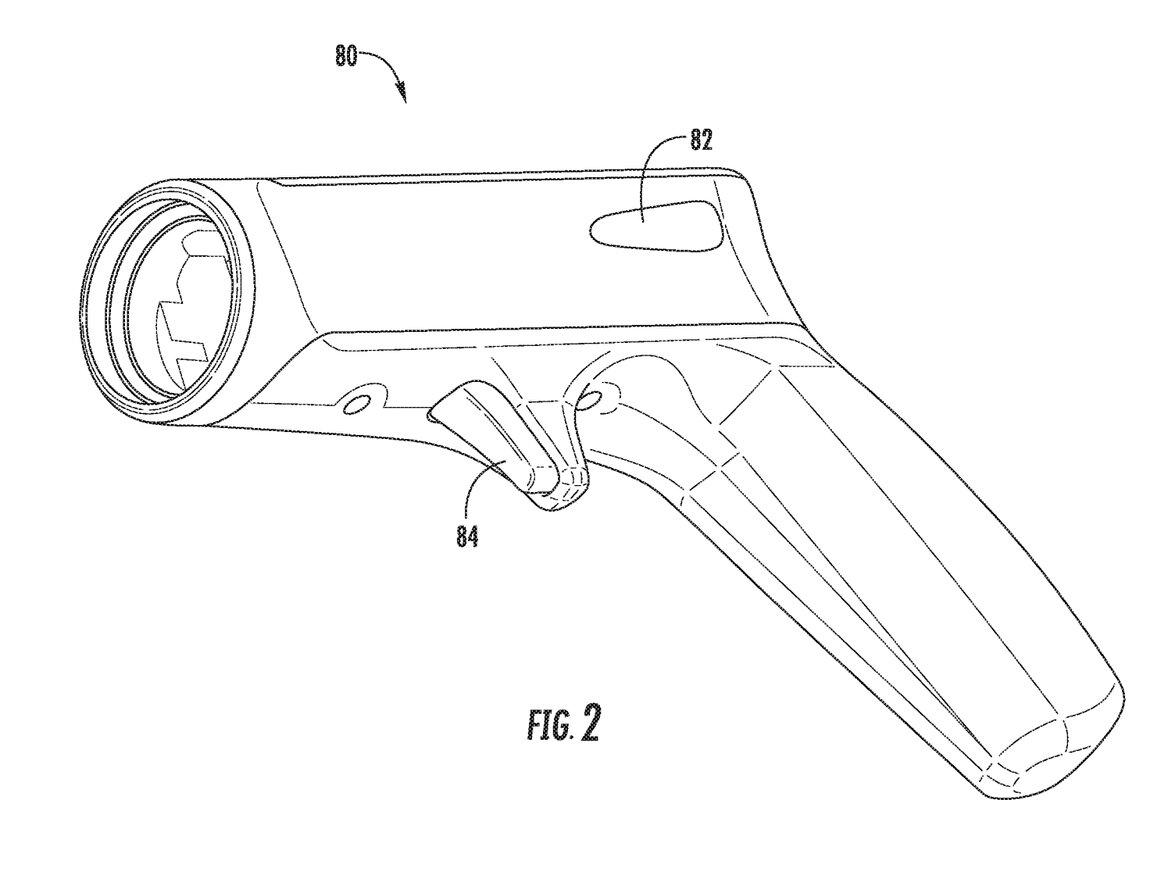
FIG. 2 is a perspective view of an input handle of the user interface of FIG. 1.

With additional reference to FIG. 2, an exemplary input handle 80 is shown in accordance with the present disclosure. It is envisioned that the input handles 80 may take a plurality of shapes and sizes. Further, the input handle 80 can include control elements specific for tools 20 associated with the respective input handle 80. For the purposes of this disclosure, the input handle 80 includes a switch 82 and an actuation control 84 (e.g., a trigger). The switch 82 is associated with the repositioning (i.e., clutching) of the input handle 80 while maintaining the position of or scaling down the motion of a tool 20 associated with the input handle 80. For example, when the switch 82 is actuated, the tool 20 maintains position within the surgical site "S" as the input handle 80 is repositioned within the workspace of the user interface 40. The actuation control 84 is associated with a function of the tool 20 (e.g., clamping, grasping, firing, opening, closing, rotating, thrusting, sealing, coagulating, cutting, slicing, etc.).

Continuing to refer to FIGS. 1 and 2, a method of actuating a tool of a robotic surgical system is described in accordance with the present disclosure. As shown in FIG. 1, the user interface 40 includes a first or right input handle 80 operably attached to a first or right control arm 60, and a second or left input handle 80' operably attached to a second or left control arm 60. During a surgical procedure, the foot pedal 90 is selectively associated with either of the right or left input handles 80, 80' to actuate a tool 20 associated with the respective one of the right or left input handles 80, 80'.

To actuate the tool 20 associated with the right input handle 80, the actuation control 84 of the right input handle 80 is actuated and released to associate the foot pedal 90 with the right input handle 80. After the foot pedal 90 is associated with the right input handle 80, the tool 20 is actuated by simultaneously depressing the foot pedal 90 and actuating actuation control 84 of the right input handle 80. It will be appreciated that the tool 20 can be actuated multiple times by depressing and holding the foot pedal 90 a single time and repeatedly actuating the actuation control 84. Alternatively, the tool 20 can be actuated multiple times by holding the actuation control 84 in an actuated position and repeatedly depressing the foot pedal 90. It is envisioned that by requiring both the depressing of the foot pedal 90 and the actuating of the actuation control 84, inadvertent actuation of the function of the tool 20 may be prevented.

In accordance with the present disclosure, once the foot pedal 90 is associated with a respective input handle (e.g., the right input handle 80), the foot pedal 90 will stay associated with the respective input handle until the actuation control 84 of another input handle (e.g., the left input handle 80') is actuated. Additionally or alternatively, the foot pedal 90 may stay associated with the respective input handle (e.g., the right input handle 80) for a predetermined time period after the actuation control 84 of the respective input handle is actuated before the foot pedal 90 is disassociated from the respective input handle. The predetermined time period may be reset with each actuation of the actuation control 84 (e.g., actuation of the tool 20). The predetermined time period may be in a range of about 15 seconds to about 2 minutes. It is also envisioned that the foot pedal 90 may disassociate from the respective input handle when the switch 82 of the respective input handle is depressed to reposition the respective input handle within the workspace of the user interface 40. When the switch 82 is released, the respective input handle may automatically reassociate with the foot pedal 90 or the actuation control 84 of the respective input handle may be required to be actuated to reassociate the respective input handle with the foot pedal 90.

It is contemplated that a variety of methods can be used to associate and disassociate the foot pedal 90 with a respective input handle. For example, the foot pedal 90 can be associated to a respective input handle by quickly actuating the actuation control 84 twice. It is contemplated that the user interface 40 may also be configured to accept voice controls to associate or disassociate the foot pedal 90 with a respective input handle. Further, the user interface 40 may include a GUI on the display 44 that allows the clinician to associate or disassociate the foot pedal 90 with a respective input handle. Additionally or alternatively, the foot pedal 90 can be disassociated from the respective input handle by releasing both the foot pedal 90 and actuation control 84 of the respective input handle and then quickly actuating, or depressing, either the foot pedal 90 or the actuation control 84 twice.

The foot pedal 90 includes an indication light 91 disposed on a surface of the foot pedal 90 that is visible to a clinician. As shown, the indication light 91 is disposed on a front surface of the foot pedal 90; however, it is envisioned that the indication light 91 could be disposed on the lever 94 or a side surface of the foot pedal 90. The indication light 91 provides visual indicia to a clinician of the status of the foot pedal 90. It is contemplated that the indication light 91 can be turned off or unilluminated when the foot pedal 90 is disassociated from the input handles 80, 80' and can be illuminated in a red color when in a locked configuration as detailed below. Alternatively, when the foot pedal 90 is disassociated from the input handles 80, 80', the indication light 91 is illuminated in a red color and when the foot pedal 90 is associated with one of the input handles 80, 80', the foot pedal 90 is illuminated in a green color. It is envisioned that the indication light 91 can indicate which input handle 80, 80' that the foot pedal 90 is associated. For example, the indication light 91 can include a right arrow that is illuminated when the foot pedal 90 is associated with the right input handle 80 and a left arrow that is illuminated when the foot pedal 90 is associated with the left input handle 80'. Additionally or alternatively, the indication light 91 can illuminate in a first color (e.g., green) when the foot pedal 90 is associated with the right input handle 80 and can illuminate in a second color (e.g., blue) different from the first color when the foot pedal 90 is associated with the left input handle 80'.

Figure 3:
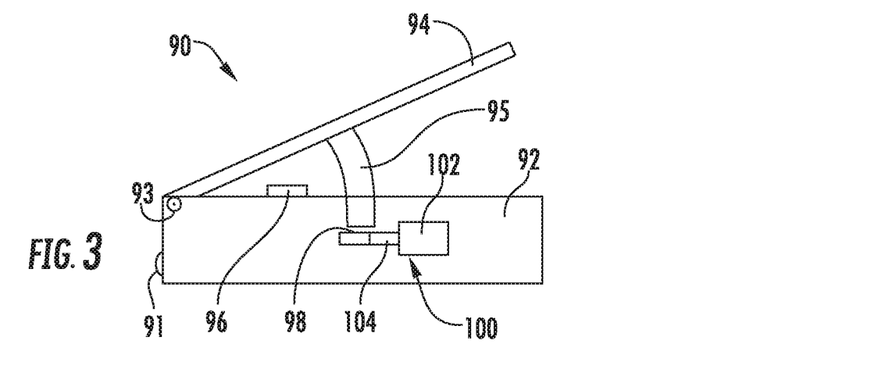
FIG. 3 is a schematic illustration of an exemplary foot pedal of the user interface of FIG. 1 in an initial position.
Figure 4:
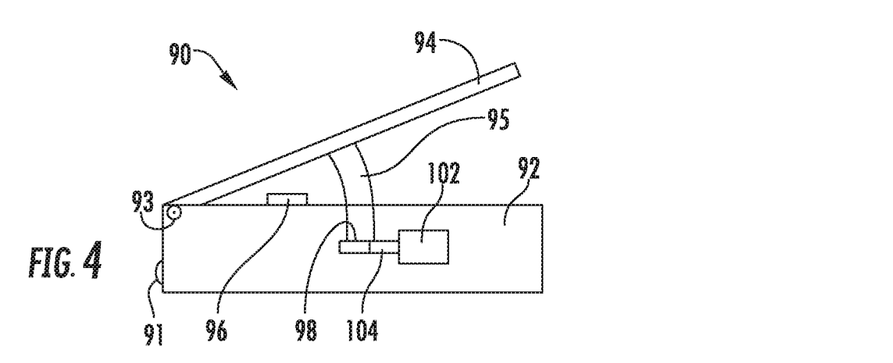
FIG. 4 is a schematic illustration of the foot pedal of FIG. 3 in a locked out position.
Figure 5:
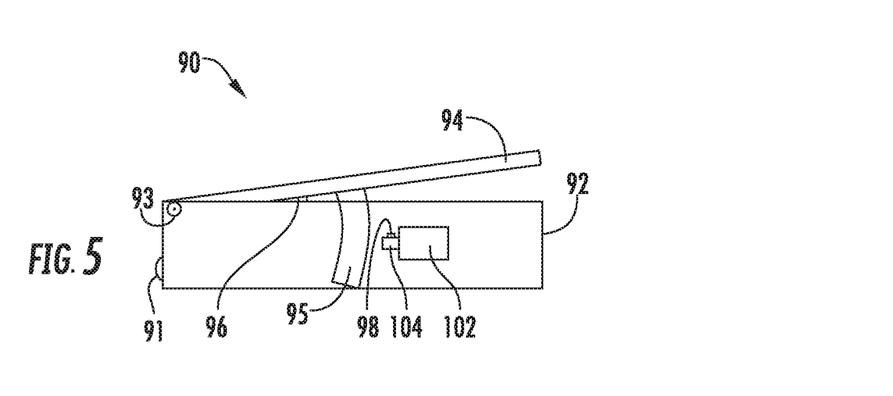
FIG. 5 is a schematic illustration of the foot pedal of FIG. 3 in an actuated position.

Referring now to FIGS. 3-5, the foot pedal 90 may include a lockout mechanism 100 that prevents the foot pedal 90 from being actuated when the foot pedal 90 is disassociated from the right and left input handles 80, 80'. The foot pedal 90 includes a frame 92, a lever 94, and an actuation switch 96. The frame 92 pivotally supports the lever 94 between an initial position (FIG. 3) and an actuated position (FIG. 5). In the initial position, the lever 94 is spaced-apart from the actuation switch 96. In the actuated position, the lever 94 is moved or pivoted such that the actuation switch 96 is depressed. For example, in FIG. 5, the lever 94 directly depresses the actuation switch 96. The actuation switch 96 is in communication with the processing unit 30 (FIG. 1) to provide a signal to the processing unit 30 when the lever 94 is in the actuated position. The actuation switch 96 may be any suitable mechanical, electrical, or electromechanical switch for detecting contact with the lever 94 or for detecting repositioning of the lever 94 between relatively far and relatively near locations (e.g., in the manner of a Hall-Effect switch).

The foot pedal 90 may include a biasing member 93 that urges the lever 94 towards the initial position. The biasing member 93 may be in the form of a torsion spring, a compression spring, etc.

With particular reference to FIG. 4, the lever 94 may also have a locked out position between the initial position and the actuated position. The foot pedal 90 includes an activation switch and the lever 94 includes a tongue 95 that extends from a lower surface of the lever 94 towards the frame 92. In the initial position, the tongue 95 of the lever 94 is spaced apart from the activation switch 98. The activation switch 98 is in communication with the processing unit 30 (FIG. 1) to provide a signal to the processing unit 30 when the tongue of the lever 94 is between the locked out position and the actuated position. The activation switch 98 may be any suitable mechanical, electrical, or electromechanical switch for detecting contact with the lever 94 or for detecting repositioning of the lever 94 between relatively far and relatively near locations (e.g., in the manner of a Hall-Effect switch).

With reference to FIGS. 3-5, the lockout mechanism 100 prevents the lever 94 from depressing the actuation switch 96 when the foot pedal 90 is not associated with an input handle (e.g., input handles 80, 80'). The lockout mechanism 100 includes a motor or solenoid 102 and a pin 104. The solenoid 102 is in communication with the processing unit (FIG. 1) and moves the pin 104 between an unlocked configuration (FIG. 3) and a locked configuration (FIG. 4). In the unlocked configuration of the pin 104, the lever 94 is pivotal between the initial position and the actuated position. In the locked configuration of the pin 104, the lever 94 is prevented from pivoting beyond the locked configuration such that the lever 94 is pivotal between the initial position and the locked out position. The processing unit 30 may prevent the pin 104 from being moved to the locked configuration when the lever 94 is beyond the locked configuration or the lever 94 may mechanically prevent the pin 104 from being moved to the locked configuration when the lever 94 is between the locked out position and the actuated position.

As detailed above, during a surgical procedure the foot pedal 90 is used to actuate a function of a tool 20 associated with a respective input handle (e.g., input handle 80, 80') of the user interface 40. Initially, the pin 104 of the lockout mechanism 100 is in the locked configuration preventing the lever 94 from being depressed. If a clinician attempts to depress the lever 94, the lever 94 pivots from the initial position to the locked out position. When the lever 94 reaches the locked out position, the pin 104 provides tactile or mechanical feedback to the clinician that the foot pedal 90 is locked out from actuating the tool 20. In embodiments including the activation switch 98, the activation switch 98 provides a signal to the processing unit 30 that the lever 94 is in the locked out position which may provide visual, audible, or tactile feedback, via the input handle 80, 80', the display 44, or the foot pedal 90, to the clinician that the actuation of the tool 20 is unavailable.

When a respective input handle (e.g., input handle 80, 80') is associated with the foot pedal 90, the processing unit 30 sends a signal to the solenoid 102 to transition the pin 104 to the unlocked configuration. When the clinician depresses the foot pedal 90, the lever 94 pivots to the actuated position and contacts the actuation switch 96. In response to the depressing of the actuation switch 96, the foot pedal 90 transmits a signal to the processing unit 30. When the actuation switch 96 of the foot pedal 90 and the actuation control 84 of the input handle 80, 80' are simultaneously providing signals to the processing unit 30, the processing unit 30 sends a control signal to the tool 20 to actuate the associated function of the tool 20.

Figure 6:
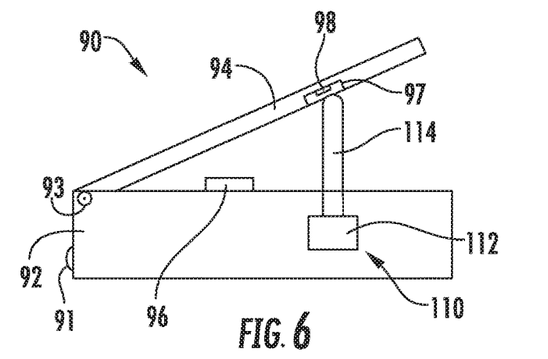
FIG. 6 is a schematic illustration of another exemplary foot pedal of the user interface of FIG. 1 in an initial position.
Figure 7:
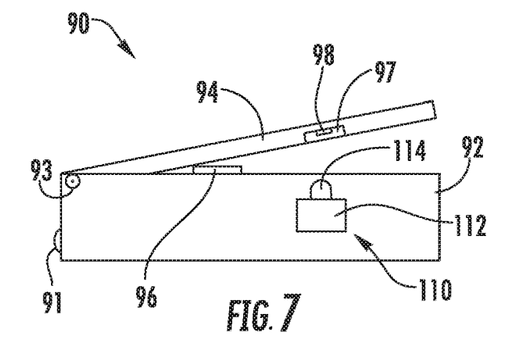
FIG. 7 is a schematic illustration of the foot pedal of FIG. 6 in an actuated position.

Referring to FIGS. 6 and 7, the foot pedal 90 includes another lockout mechanism 110 in accordance with the present disclosure including a solenoid 112 and a pin 114. The solenoid 112 and the pin 114 of the lockout mechanism 110 are similar to the solenoid 102 and the pin 104 of the lockout mechanism 100, as such only the differences will be described for reasons of brevity.

The solenoid 112 is positioned within the frame 92 of the foot pedal 90 and the pin 114 extends from the solenoid 112 towards a lower surface of the lever 94. The lever 94 defines a retaining well 97 to receive the pin 114. In an unlocked configuration of the pin 114, the pin 114 is substantially within the frame 92 such that the lever 94 is pivotal to the actuated position. In the locked configuration of the pin 114, the pin 114 is extended by the solenoid such that the pin 114 prevents the lever 94 from pivoting beyond the locked configuration. When the lever 94 is in the locked configuration and the pin 114 is in the locked configuration, the pin 114 is engaged with the well 97 of the lever 94. During a surgical procedure, if the pedal 90 is between the locked out position and the actuated position without an input handle associated with the foot lever 94, the solenoid 112 extends the pin 114 into the well 97 of the lever 94 to pivot the lever 94 to the locked out position. As the solenoid 112 extends the pin 114, the lever 94 may move a foot of a clinician to provide tactile feedback that the respective input handle is no longer associated with the foot lever 94.

Figure 8:
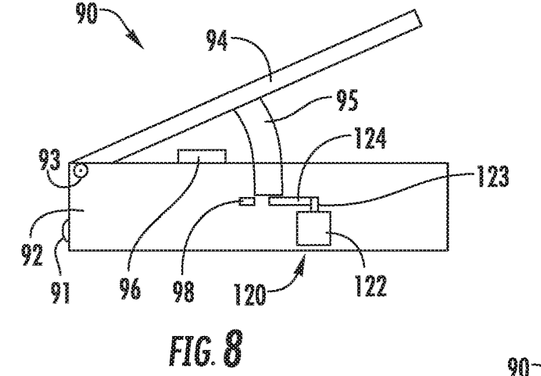
FIG. 8 is a schematic illustration of another exemplary foot pedal of the user interface of FIG. 1 in an initial position.
Figure 9:
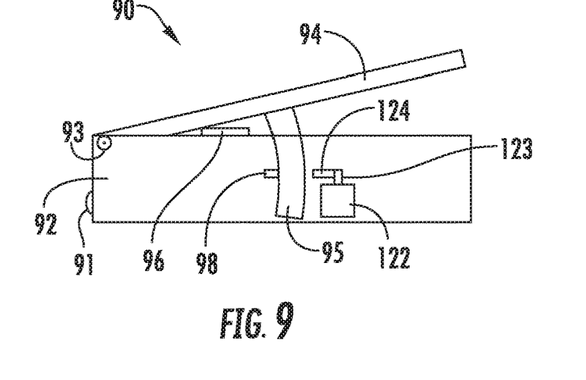
FIG. 9 is a schematic illustration of the foot pedal of FIG. 8 in an actuated position.

Referring to FIGS. 8 and 9, the foot pedal 90 includes another lockout mechanism 120 provided in accordance with the present disclosure including a motor 122 and a pin or tab 124. The motor 122 is mounted to the frame 92 with the tab 124 rotatably coupled to a drive shaft 123 of the motor 122. The tab 124 is rotatable between a locked configuration and an unlocked configuration. In the locked configuration (FIG. 8), the motor 122 positions the tab 124 such that the tab 124 prevents the lever 94 from pivoting beyond the locked out position. It is envisioned that the tab 124 may be biased towards the locked configuration. In the unlocked configuration (FIG. 9), the tab 124 is positioned to permit the lever 94 to pivot between the initial position and the actuated position. The motor 122 is configured to rotate the tab 124 between the locked configuration and the unlocked configuration.

Figure 10:
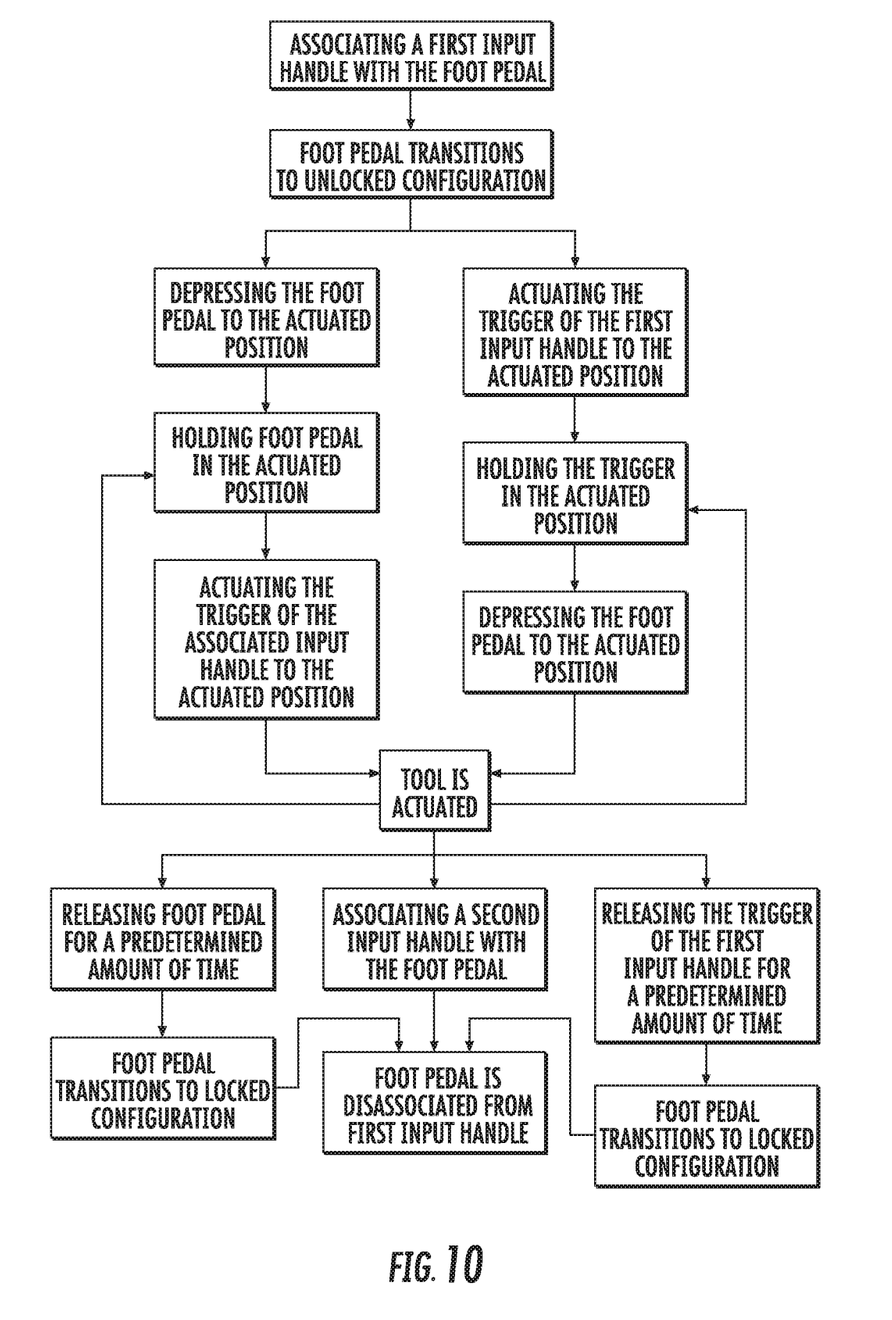
FIG. 10 is a flowchart illustrating a method of controlling a function of a tool of a robot system with a user interface in accordance with the present disclosure.

With reference to FIG. 10, an exemplary method for actuating a tool of a surgical robot with a foot pedal is illustrated in accordance with the present disclosure. Initially, an input handle is associated with the foot pedal. When the foot pedal is associated with the input handle, the foot pedal transitions to an unlocked configuration. The foot pedal and the input handle are then simultaneously depressed to actuate the tool. The tool can be actuated multiple times by simultaneously depressing the foot pedal and input handle multiple times as detailed above. The foot pedal is then disassociated from the input handle by releasing either the foot pedal or a trigger of the input handle for a predetermined amount of time or associating another input handle with the foot pedal.

Figure 11:
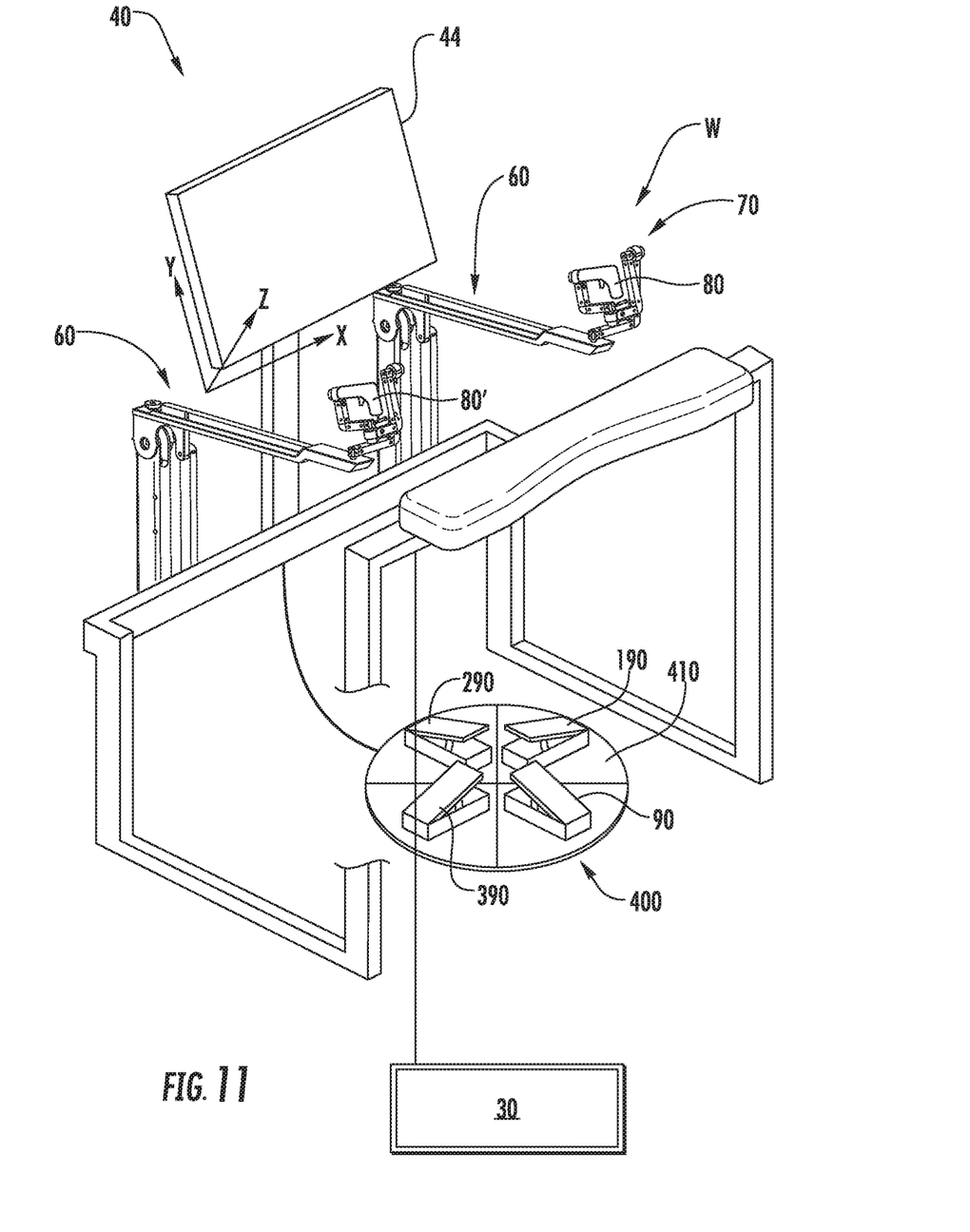
FIG. 11 is a schematic illustration of a user interface with an exemplary pedal assignment mechanism in accordance with the present disclosure.

With reference to FIG. 11, an exemplary embodiment of the user interface 40 includes a pedal assignment mechanism 400 in accordance with the present disclosure. The pedal assignment mechanism 400 includes a rotary table 410 that supports pedals 90, 190, 290, 390. Each of the pedals 90, 190, 290, 390 is similar to the pedal 90 and will not be detailed individually in favor of brevity.

The rotary table 410 is in communication with the processing unit 30 (FIG. 1) such that the rotary table 410 rotates in response to a signal from the processing unit 30. The processing unit 30 rotates the rotary table 410 such that a selected one of the foot pedals 90, 190, 290, 390 is accessible to the clinician such that when the selected one of the foot pedals 90, 190, 290, 390 is associated with one of the input handles 80, 80', the selected one of the foot pedals 90, 190, 290, 390 actuates a function of a tool 20 (FIG. 1) assigned to the associated input handle 80, 80'.

The clinician can select which one of foot pedals 90, 190, 290, 390 to associate with the input handle 80 by interacting with the user interface 40. For example, the user interface 40 can accept voice commands and/or include a GUI on the display 44 that allows the clinician to selected one of the foot pedals 90, 190, 290, 390. Additionally or alternatively, the processing unit 30 can detect a tool 20 (FIG. 1) which is coupled to an arm 12 of the surgical robot 10 and select a foot pedal 90, 190, 290, 390 that corresponds to the detected tool 20.

Figure 12:
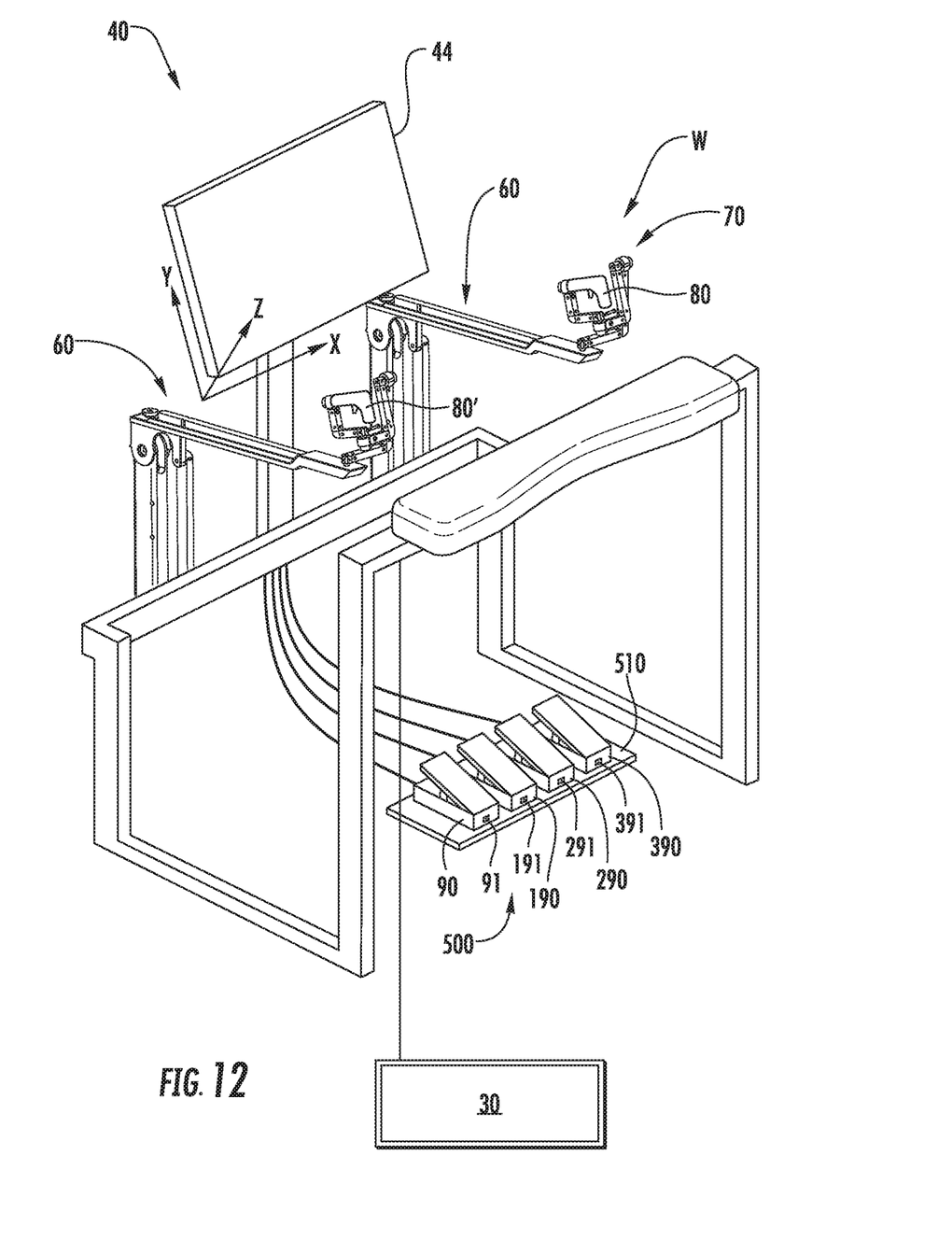
FIG. 12 is a schematic illustration of a user interface with another exemplary pedal assignment mechanism in accordance with the present disclosure.

Referring now to FIG. 12, another exemplary embodiment of the user interface 40 includes a pedal assignment mechanism 500 in accordance with the present disclosure. The pedal assignment mechanism 500 includes a rack 510 that supports pedals 90, 190, 290, 390.

The rack 510 is in communication with the processing unit 30 (FIG. 1) such that an indication light 91, 191, 291, 391 on an associated foot pedal 90, 190, 290, 390 provides an indication that the foot pedal 90, 190, 290, 390 is associated with an input handle 80, 80' in response to a signal from the processing unit 30. The selected one of the foot pedals 90, 190, 290, 390 actuates a function of a tool 20 (FIG. 1) assigned to the associated input handle 80, 80'. As shown, the rack 510 includes a single tier with all four foot pedals 90, 190, 290, 390; however, it is contemplated the rack 510 can include multiple tiers with one or more foot pedals on each tier.

The clinician can select which one of foot pedals 90, 190, 290, 390 to associate with the input handle 80 by interacting with the user interface 40. For example, the user interface 40 can accept voice commands and/or include a GUI on the display 44 that allows the clinician to select one of the foot pedals 90, 190, 290, 390. Additionally or alternatively, the processing unit 30 can detect a tool 20 (FIG. 1) which is coupled to an arm 12 of the surgical robot 10 and select a foot pedal 90, 190, 290, 390 that corresponds to the detected tool 20.

Figure 13:
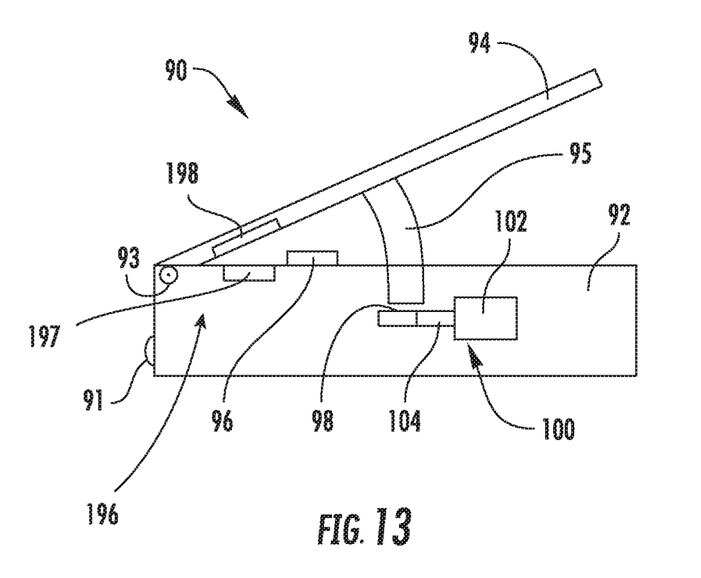
FIG. 13 is a schematic illustration of the foot pedal of FIG. 3 including an actuation sensor system.

With reference to FIG. 13, the foot pedal 90 may include an actuation sensor system 196 in place of or in addition to the actuation switch 96 (FIG. 3). The actuation sensor system 196 determines the amount of actuation or the position of the lever 94 relative to the frame 92. Determining the amount of actuation or the position of the lever 94 may allow for additional control of a tool associated with the foot pedal 90, e.g., tool 20.

Additionally or alternatively, the amount of actuation or the position of the lever 94 may be used to manipulate light emitted from the indication light 91. For example, an intensity of the indication light 91 may progressively increase as the lever 94 is actuated towards the frame 92. In some embodiments, a color of the indication light 91 changes as a position of the lever 94 changes. For example, the indication light 91 may be green when the lever 94 is in the initial position and may gradually change to red as the lever 94 is moved towards the actuated position. In some embodiments, the color of the indication light 91 changes discreetly from green in the initial position, yellow when actuated between the initial position and the actuated position, and red in the actuated position. In certain embodiments, the pattern of the indication light 91 may vary in response to the position of the lever 94. For example, the indication light 91 may be solid when the lever 94 is in the initial position and may begin to slowly flash as the lever 94 is moved towards the actuated position. As the lever 94 approaches the actuated position, the frequency of the flashing of the indication light 91 may increase.

The actuation sensor system 196 includes a first element 197 disposed within the frame 92 of the foot pedal 90 and a second element 198 disposed within the lever 94 of the foot pedal 90. In some embodiments, the first element 197 is disposed on a surface of the frame 92 and may be disposed between the frame 92 and the lever 94. In embodiments, the second element 198 may be disposed on a surface of the lever 94 and may be disposed on a surface of the lever 94 between the lever 94 and the frame 92.

In particular embodiments, the first element 197 is a capacitive sensor and the second element 198 is configured to be detected by the first element 197 such that the actuation sensor system 196 is a capacitive displacement system. The second element 198 may be formed of a conductive material or a non-conductive material.

In certain embodiments, the second element 198 is configured to generate a magnetic or electrical field that is detectable by the first element 197. For example, the second element 198 may be a magnet and the first element 197 may be a Hall Effect sensor that detects a magnetic field generated by the second element 198 to determine a distance of the second element 198 from the first element 197.

In some embodiments, the first and second elements 197, 198 are each electrodes with an electromagnetic field generated therebetween. The strength of the electromagnetic field is indicative of a distance between the first and second elements 197, 198.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A foot pedal for a user interface of a robotic surgical system, the foot pedal comprising:
 a frame;
 a lever coupled to the frame, the lever pivotable relative to the frame between an initial position and a fully actuated position;
 a sensor system having a first element associated with the frame and a second element associated with the lever, the sensor system configured to determine the position of the lever relative to the frame; and
 a lockout mechanism configured to transition between a locked configuration and an unlocked configuration based on whether the foot pedal is associated with an input handle.

2. The foot pedal according to claim 1, further comprising an actuation switch, the lever configured to depress the actuation switch when the lever is in the fully actuated position.

3. The foot pedal according to claim 1, wherein the first element is disposed within the frame.

4. The foot pedal according to claim 1, wherein the second element is disposed within the lever.

5. The foot pedal according to claim 1, wherein the frame includes an indication light configured to emit light from the frame.

6. The foot pedal according to claim 5, wherein the indication light is configured to vary a property of the emitted light in response to the position of the lever relative to the frame.

7. The foot pedal according to claim 6, wherein the property of the emitted light is at least one of a color, an intensity, or a pattern.

8. The foot pedal according to claim 1, wherein the sensor system is a capacitive displacement system.

9. The foot pedal according to claim 8, wherein the second element is a conductive material.

10. The foot pedal according to claim 1, wherein the second element is configured to generate at least one of a magnetic field or an electrical field and the first element is configured to detect the at least one of the magnetic field or the electrical field.

11. A user interface of a robotic surgical system, the user interface comprising:
 a processing unit;
 an input handle including an actuation control, the actuation control having an activated position in which the input handle transmits a handle signal to the processing unit; and
 a foot pedal including:
  a frame;
  a lever coupled to the frame, the lever pivotable relative to the frame between an initial position and a fully actuated position;
  a sensor system having a first element associated with the frame and a second element associated with the lever, the sensor system configured to transmit the position of the lever relative to the frame to the processing unit; and
  a lockout mechanism configured to transition between a locked configuration and an unlocked configuration based on whether the foot pedal is associated with the input handle.

12. The user interface according to claim 11, wherein the foot pedal includes an actuation switch, the lever configured to depress the actuation switch when the lever is in the fully actuated position, the actuation switch configured to transmit an actuation signal to the processing unit when the actuation switch is depressed.

13. The user interface according to claim 11, wherein the lockout mechanism prevents movement of the foot pedal from the initial position to the fully actuated position when the lockout mechanism is in the locked configuration and the lockout mechanism allows movement of the foot pedal between the initial position and the fully actuated position when the lockout mechanism is in the unlocked configuration.

14. The user interface according to claim 11, wherein the frame includes an indication light configured to emit light from the frame.

15. A method of manipulating a robotic surgical system having a user interface, the method comprising:
 depressing a lever of a foot pedal of the user interface towards a frame of the foot pedal from an initial position towards a fully actuated position;

visualizing an indication light of the frame to determine the position of the lever relative to the frame; and locking the foot pedal when the foot pedal is not associated with an input handle.

16. The method according to claim 15, further comprising associating an input handle of the user interface with the foot pedal of the user interface.

17. The method according to claim 15, wherein visualizing the indication light of the frame includes a sensor system of the foot pedal determining a position of the lever relative to the frame, the indication light varying a property of light emitted therefrom in response to the position of the lever determined by the sensor system.

18. The method according to claim 17, wherein determining the position of the lever relative to the frame includes a first element associated with the frame detecting a position of a second element associated with the lever.

19. The method according to claim 18, wherein detecting the position of the second element includes the first element being a capacitive sensor that detects the position of the second element.

20. The method according to claim 18, wherein detecting the position of the second element includes detecting a magnetic field generated by the second element.

\* \* \* \* \*